United States Patent
Shearer et al.

(10) Patent No.: US 11,933,288 B2
(45) Date of Patent: Mar. 19, 2024

(54) DISPENSER CASSETTE FOR USE IN A PERISTALTIC PUMP

(71) Applicant: Integra Biosciences AG, Zizers (CH)

(72) Inventors: Daniel Shearer, Pratval (CH); Noel Pasquier, Landquart (CH); Andreas Staedler, Felsberg (CH)

(73) Assignee: Integra Biosciences AG, Zizers (CH)

( * ) Notice: Subject to any disclaimer, the term of this patent is extended or adjusted under 35 U.S.C. 154(b) by 98 days.

(21) Appl. No.: 17/467,639

(22) Filed: Sep. 7, 2021

(65) Prior Publication Data

US 2022/0074405 A1 Mar. 10, 2022

(30) Foreign Application Priority Data

Sep. 8, 2020 (CH) ..................................... 01112/20

(51) Int. Cl.
*F04B 43/08* (2006.01)
*A61M 39/10* (2006.01)
*F04B 43/12* (2006.01)

(52) U.S. Cl.
CPC ......... *F04B 43/086* (2013.01); *A61M 39/105* (2013.01); *F04B 43/1292* (2013.01)

(58) Field of Classification Search
CPC .... F04B 43/12; F04B 43/0072; F04B 43/086; A61M 39/105
See application file for complete search history.

(56) References Cited

U.S. PATENT DOCUMENTS

| | | | |
|---|---|---|---|
| 4,184,815 A | 1/1980 | Casson et al. | |
| 4,432,707 A * | 2/1984 | Anderson | F04B 43/1253 417/DIG. 1 |
| 4,537,561 A * | 8/1985 | Xanthopoulos | A61M 5/14232 D24/111 |
| 6,494,692 B1 | 12/2002 | Green | |
| 6,871,015 B2 * | 3/2005 | Gutierrez | B67D 7/80 222/325 |
| 7,118,203 B2 * | 10/2006 | Davis | F04B 43/1284 347/85 |
| D826,284 S * | 8/2018 | Mead | D15/7 |
| 2005/0047946 A1* | 3/2005 | Davis | B41J 2/17596 417/477.11 |
| 2008/0085200 A1* | 4/2008 | Michels | F04B 43/1253 417/477.1 |

FOREIGN PATENT DOCUMENTS

| | | | | |
|---|---|---|---|---|
| EP | 3 561 551 | | 10/2019 | |
| GB | 2467605 A | * | 8/2010 | ............ A61M 39/08 |

OTHER PUBLICATIONS

Quantum Pump (https://www.youtube.com/watch?v=kg2UFFvvKww, dated Jul. 11, 2017) (Year: 2017).*

(Continued)

*Primary Examiner* — Nathan C Zollinger
(74) *Attorney, Agent, or Firm* — Andrus Intellectual Property Law, LLP

(57) ABSTRACT

A dispenser cassette is shown and described for attachment to a peristaltic pump that has a first cartridge, second cartridge, and tubes, which are accommodated in the dispenser cassette such that both ends of the tubes are each inserted into one of the cartridges. According to the invention, the two cartridges are connected to one another by an elastic connector.

15 Claims, 3 Drawing Sheets

(56) References Cited

OTHER PUBLICATIONS

Renu SU Technology Cartridge (https://www.wmfts.com/siteassets/catalog/products/corporate/watson-marlow-pumps/pumpheads/15415/literature/wd-wm-renu-sterility-en.pdf, 2019). (Year: 2019).*
European Search Report dated Mar. 9, 2021 in priority Switzerland Patent Application 01112/20.
Watson Marlow Pumps brochure (https://www.wmftg.com).

* cited by examiner

DISPENSER CASSETTE FOR USE IN A PERISTALTIC PUMP

CROSS REFERENCE TO RELATED APPLICATION

The present application claims priority to Switzerland Patent Application 01112/20 filed Sep. 8, 2020.

TECHNICAL FIELD OF THE INVENTION

The invention relates to a dispenser cassette for use in a peristaltic pump according to the preamble of claim 1.

BACKGROUND OF THE INVENTION

Dispenser cassettes known from the prior art for use in a peristaltic pump have a three-part construction. The dispenser cassette comprises three cartridges and continuous tubes, each of which starts at the first cartridge, passing through the second cartridge into the third cartridge (see FIG. 1). The tubes form the only connection between the cartridges. The number of tubes in a dispenser cassette, which are arranged adjacently in a row, parallel to one another, is 8 or 16. The tubes between the first and second cartridge end up on the rotor in a peristaltic pump. Because the tubes between the first and second cartridge are on the rotor, and therefore exposed to greater demands, these tubes can be provided separately, and do not need to extend all the way from the first cartridge to the third cartridge. In addition to the tubes, dispenser tips are also attached to the first cartridge, which then convey the medium in the tubes to the exterior. With a dispenser cassette known from the prior art, each cartridge must be attached individually to the peristaltic pump. With a three-part construction, this results in three steps that must be carried out successively, both when attaching and removing peristaltic pumps.

The tubes used in a dispenser cassette must have a flexible outer wall. The medium is conveyed in the tubes through peristalsis. This means that the medium is conveyed in a targeted direction by to the movement of the tube. The tubes in the dispenser cassette must be tightened onto the rotor to a certain extent, in order that the tube can be deformed by the rotor.

Setting the tension for each tube, as well as attaching the cartridges individually, results in a complicated production process as well as a complicated installation of these dispenser cassettes on a peristaltic pump. This results in longer production times, further reflected in an inefficient production process.

U.S. D 826 284 S discloses a design for a dispenser cassette for use in a peristaltic pump. The drawings in the design application show two cassettes, which are connected via a U-shaped connector. Tubes are placed in this U-shaped connector, between the cassettes. The tubes each open into a collecting tube, which are placed longitudinally in both cartridges. It can be derived from the product description by the applicant that the apparatus enables dosing with nearly no pulsations.

OBJECT

The object of the present invention is therefore to create an alternative dispenser cassette, which can be operated more easily than those from the prior art.

DESCRIPTION

This object is achieved with a dispenser cassette that is to be attached to a peristaltic pump, which has a first cartridge, second cartridge, and tubes, which are placed in the dispenser cassette such that each of the ends of the tubes are inserted in a cartridge. The second cartridges are connected to one another by an elastic connector. The first cartridge has holes for the dispenser tips, and the nozzles are placed on the ends of the tubes.

Aside from the tubes, the dispenser cassettes comprising the elastic connector and the two cartridges forms an integral component. The elastic connector results in a permanent connection between the cartridges, regardless of whether a tube is located between the cartridges. Because of the elasticity of the connector, the cartridges can move in relation to one another to a certain extent. The extent of this movement is determined by the design of the connector. The connector can enable both translatory and rotational movements of the cartridges in relation to one another. The connector also protects the tubes. As a result, the tubes are not subjected to any loads other than those for fulfilling their function of conveying the medium through peristalsis. The elasticity of the connector also results in a certain flexibility, such that the dispenser cassettes can be used with peristaltic pumps of different designs and shapes.

The dispenser cassette is intended for use with a peristaltic pump. The dispenser cassettes aid the peristaltic pumps in conveying and discharging a liquid medium in a targeted manner. The liquid medium is ideally discharged via nozzles. These enable a more precise dosing of the medium. The medium should be conveyed from the tube into the nozzle without any additional resistance. For this reason, holes are formed in the first cartridge. These holes define a point where the nozzle is to be attached to obtain a transference of the medium from the tube to the nozzle with as little resistance as possible.

In the framework of this application, the term "cartridge" is understood to mean a device for receiving one or more tubes. The tube can be guided through the cartridge, or it can terminate inside the cartridge. The cartridge makes it possible to place the tubes precisely in a peristaltic pump, such that movement of the tubes is prevented within the cartridge. The cartridge also makes it possible for the rotor to move the tubes in a peristaltic manner synchronously.

In a preferred embodiment, the elastic connector is U-shaped, and a cartridge is attached to each end. The U-shape of the connector results in a certain elasticity. With the appropriate materials, the connector can behave in an elastic manner simply due to its U-shape. A connector produced in this manner can be manufactured easily, also resulting in lower production costs.

The cartridges on the ends of the connector are advantageously parallel to one another. The elastic connector is therefore located between two longitudinal sides of the cartridges. With this design, the width of the dispenser cassette can be determined by the length of the cartridges.

In another preferred embodiment, the tubes are releasably attached to the two cartridges. The tubes are responsible for conveying a medium in a peristaltic pump. Because of the loads the tubes are subjected to, they have a shorter service life than the cartridges with the elastic connector in the dispenser cassette. As a result, the dispenser cassette can still be used after removing the tubes and attaching new tubes to the two cartridges. The tubes also do not necessarily have to be replaced only at the end of their service lives. It is also possible to replace the tubes quickly if different demands require tubes of different sizes or shapes. The tubes are preferably connected to the cartridges in a form-fitting manner. Holes can be provided on the cassettes for this. This form-fitting connection makes it possible to quickly connect and release them.

The first cartridge preferably has the same number of holes for tubes and nozzles. A nozzle is preferably located at the downstream end of each tube. As a result, the medium that is to be dispensed is transported separately in each of the tubes, and conveyed outward via the respective nozzles. The dispenser cassette is intended to be operated with tubes with nearly equal diameters. Because of these basically identical diameters of the tubes used in the dispenser cassettes, there is no need for a collecting tube or tank downstream of the tubes. The collecting tube downstream of the tubes minimizes the differences in the amounts that are conveyed between the tubes and the resulting pulsations. Because the nearly identical diameters of the tubes in this embodiment results in the amounts conveyed between the tubes also being nearly identical, the medium can be conveyed outward from each individual tube via a downstream nozzle. This makes it easier to operate, and results in greater freedom in the use of the dispenser cassettes. The tubes in the dispenser cassettes are preferably curved in a U-shape. The medium is conveyed in a peristaltic pump by deforming the tubes with the rotor in the peristaltic pump. For the rotor to be able to deform the tubes, the tubes must be tightened over the rotor. The cartridges in the dispenser cassette therefore end up on nearly opposite longitudinal sides of the rotor. In addition to enabling the conveyance of the liquid medium in the tubes through peristalsis, the tightening of the tubes also makes it possible to close them off. Because the tubes lie on a rotor in the dispenser cassette, it makes sense for them to be curved in a U-shape. The load to the tubes can also be adjusted by altering the curvature. Different rotor designs can be used in the peristaltic pumps. As a result, it is conceivable to take different rotors into account in designing the dispenser cassettes, and to adapt the curvature of the tubes to the respective rotor.

The tubes are preferably located within the U-shaped connector. An inner portion of the connector is formed by the U-shape thereof, formed by the connector itself and the imaginary connecting line between the cartridges attached to both ends thereof. The tubes can preferably lie within the connector. As a result, the elastic connector protects the tubes, so that they can only be accessed through the interior of the U-shaped connector. Access to the tubes from the outside is therefore prevented. As a result, the dispenser cassette can be held without coming in contact with the tubes, thus potentially damaging them. At the same time, the tubes are not subjected to unintentional compression pressures in this constellation. The tubes can only be subjected to tensile forces to the extent allowed by the connector.

In another preferred embodiment, the second cartridge is intended to receive one or more supply tubes, wherein the supply tube conveys the medium to be transported to the dispenser cassette. Because the supply tubes are not exposed to the same demands that the tubes in the dispenser cassette are exposed to, they do not need to be as sturdy.

The number of supply tubes is advantageously equal to the number of tubes between the cartridges in the dispenser cassette, such that the contents of a supply tube in the second cartridge can be delivered to a tube. The same number of supply tubes facilitates transportation of the medium to the dispenser cassette in equal quantities. As a result, the medium does not have to be branched off into an individual tube, thus minimizing the flow resistance for the medium.

In another preferred embodiment, the dispenser cassette can have a distributor prior to the second cartridge. The distributor receives the medium and distributes and transports it to the tubes in the second cartridge through channels in the distributer. The distributer may have one or more receiving holes. The number of channels is preferably the same as the number of tubes on the dispenser cassette, such that each tube can be assigned a supply channel.

In another preferred embodiment, the dispenser cassette can be up to 15 cm wide, and can be operated with one hand. The permanent connection between the cartridges obtained with the elastic connector results in a single, integral component. The one-handed operation of the dispenser cassette is enabled by limiting the width of the dispenser cassette to 15 cm, because of this integral construction. The dispenser cassette can therefore be attached to and released from the peristaltic pump more quickly. The width of the dispenser cassette is measured at a right angle to the connecting line between the cartridges.

The dispenser cassette advantageously comprises an RFID module that can communicate with the peristaltic pump. An RFID module can contain relevant data for operating the peristaltic pump. This data can comprise the pump factor for the dispenser cassette. This factor is dependent on the tubes in the dispenser cassette and the amount of medium that is to be conveyed under certain boundary conditions.

The dispenser cassette can contain data relevant to the operation thereof in the RFID module. This data is sent to the peristaltic pump by means of the RFID module when the dispenser cassette is attached thereto. As a result, the parameters for conveying the medium can be set in the peristaltic pump on the basis of the data obtained from the RFID module in the dispenser cassette. Without the RFID, the parameters would have to be set for the peristaltic pump manually.

The dispenser cassette can preferably accommodate up to 32 tubes. This means that 32 tubes are attached to each of the two cartridges. The tubes can all be in one plane, or they can be offset to one another. When they are offset, they can collectively form a round or rectangular cross section.

The ends of the tubes are preferably reinforced where they are inserted into the holes in the cartridges. These holes can be formed in the cartridges during the production thereof or in a subsequent process. The shape of the holes must fit the shape of the reinforcement of the tube. The holes allow the tubes to be attached to the cartridges without additional tools. The reinforcements can be obtained in a number of ways. One means is through molding. It is also possible to produce the tubes in an extrusion process without reinforcement, and to subsequently glue the reinforcement to the tube.

These reinforcements are formed on the ends of the tubes. They can also be formed at a distance to the end of the tube. The maximum distance to the end of the is $\frac{1}{10}$ of the length of the tube.

The tubes are advantageously parallel to one another in the dispenser cassette. This prevents the tubes from crossing one another. The tubes thus remain in alignment, ensuring that the tubes are not exposed to further loads.

This parallel arrangement also ensures that each tube extends over the same distance from the first cartridge to the second cartridge. This is of particular importance because the resistance the liquid medium is subjected to depends on the length of the tube, such that tubes of different lengths result in different conveyance amounts.

In another embodiment, the tubes are permanently attached to the cartridges. The tubes are therefore permanently connected to each of the cartridges. This results in an integrally formed dispenser cassette. One advantage of an integral dispenser cassette is that one dispenser cassette can be easily replaced with another dispenser cassette. Because the tubes are part of the dispenser cassette, a corresponding conveyance amount can be assigned to the dispenser cassettes as such, without having to take the tubes into account. This may have the advantage of being able to use and exchange a dispenser cassette more quickly when in operation. This also results in a major advantage regarding the production thereof. Because of the integral construction of the dispenser cassettes with tubes, they can be produced automatically. As a result, it is possible to produce a larger number within the same period of time, thus reducing the production costs per piece.

The tubes are preferably materially bonded to the two cartridges. The type of material bonding depends largely on the materials that are used. If different plastics are used, the material bond can be initiated during an injection molding process or melting process during the production thereof. These tubes can also conceivably be molded onto the dispenser cassette, such that the connection of the tubes to the dispenser cassette is obtained via the two cartridges. As a result, the connection of the tubes to the cartridges can take place at the same time as the production of the cartridges and the elastic connector. This results in shorter production times, and the conveyance amount for the dispenser cassette can be clearly designated based on the permanent connection between the tubes and the cartridges.

Both cartridges advantageously have at least one projection protruding in the longitudinal direction on the sides perpendicular to the longitudinal direction. This projection can serve as a latching element. The longitudinal direction is defined by the direction in which the tubes are arranged adjacently. This protruding projection, or latching element, is used to connect the dispenser cassette to a peristaltic pump. In one extremely simple embodiment, the dispenser cassette can be connected to the peristaltic pump in a form-fitting connection via the projection or latching element. As a result, the dispenser cassette can be easily installed on the peristaltic pump with just one hand.

DETAILED DESCRIPTION OF THE DRAWINGS

The same reference symbols are used below for identical or functionally identical elements (in the different figures). An additional apostrophe may be used to distinguish similar or functionally identical or similar elements in another embodiment.

Figure 1:
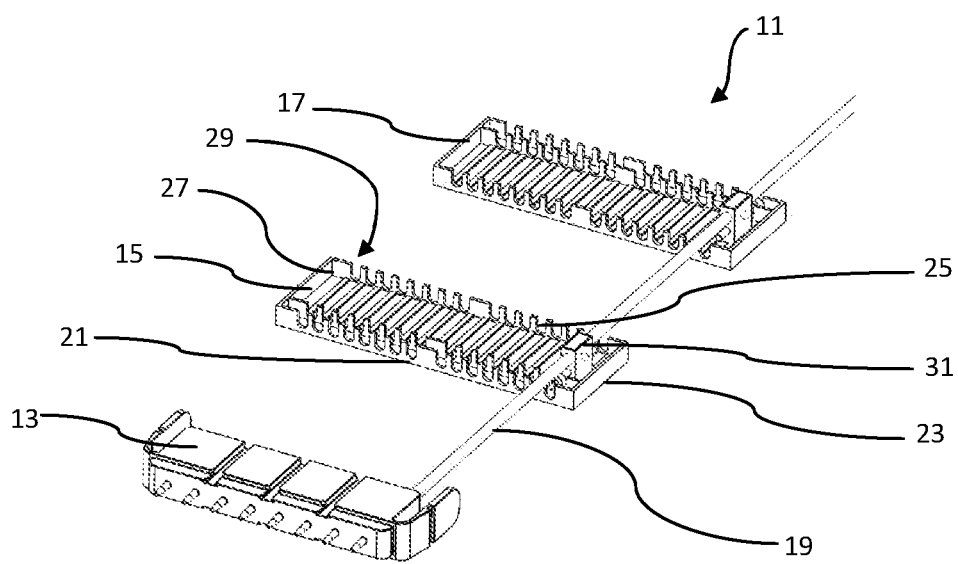
FIG. 1 shows a three-dimensional view of a three-part dispenser cassette from the prior art.

A dispenser cassette 11 from the prior art is shown in FIG. 1. The dispenser cassette 11 comprises three cartridges 13, 15, 17, which are connected to one another in this illustration by just one tube 19. The cartridges 13, 15, 17 are box-shaped. The width 23 is parallel to the axial direction of the tubes 19. The width 23 and the distance between the cartridges is selected such that the tubes 19 can be bent 180° between two cartridges, without affecting the flow through the tubes 19. The length 21 of the cartridges is determined by the number of tubes 19 that are to be accommodated. Because the tubes 19 are parallel along the width 23, the length 21 of the cartridge depends directly on the number of tubes 19 that it is to accommodate. The height of the cartridge is also determined by the tubes. This height is slightly higher than the outer diameter of the tubes, plus from the wall thickness of the cartridge. There are 25 placements on the first and second opposing narrow sides. These narrow sides are each defined by a longitudinal edge and a vertical edge. Each cartridge 13, 15, 17 comprises two parts, a container 27 and a lid. Only the containers 27 for the three cartridges are shown in FIG. 1. The lid can be a flat element on the container 27, wherein the edges formed by the longitudinal edge 21 and the width of the container 27 define the surface area of the lid. Because the cartridge has two parts, the tubes can be placed in the cartridge. Because of this, the container 27 must contain an opening 29 that allows free access to all of the tubes placed therein. This opening 29 is then closed by the lid for the cartridge after the tubes have been placed in the container 27. There is a tensioning element 31 for each tube in the second and third cartridges 15, 17, wherein just one tube 19 is shown in FIG. 1, with the respective tensioning element 31. The tensioning element 31 can be operated using a set screw. The tension acting on the tube 19 can then be varied using the tensioning element 31. This is necessary for adjusting the internal diameter of the tube 19 by altering the tension applied thereto, because the tubes 19 may have different internal diameters due to high production tolerances.

Figure 2:
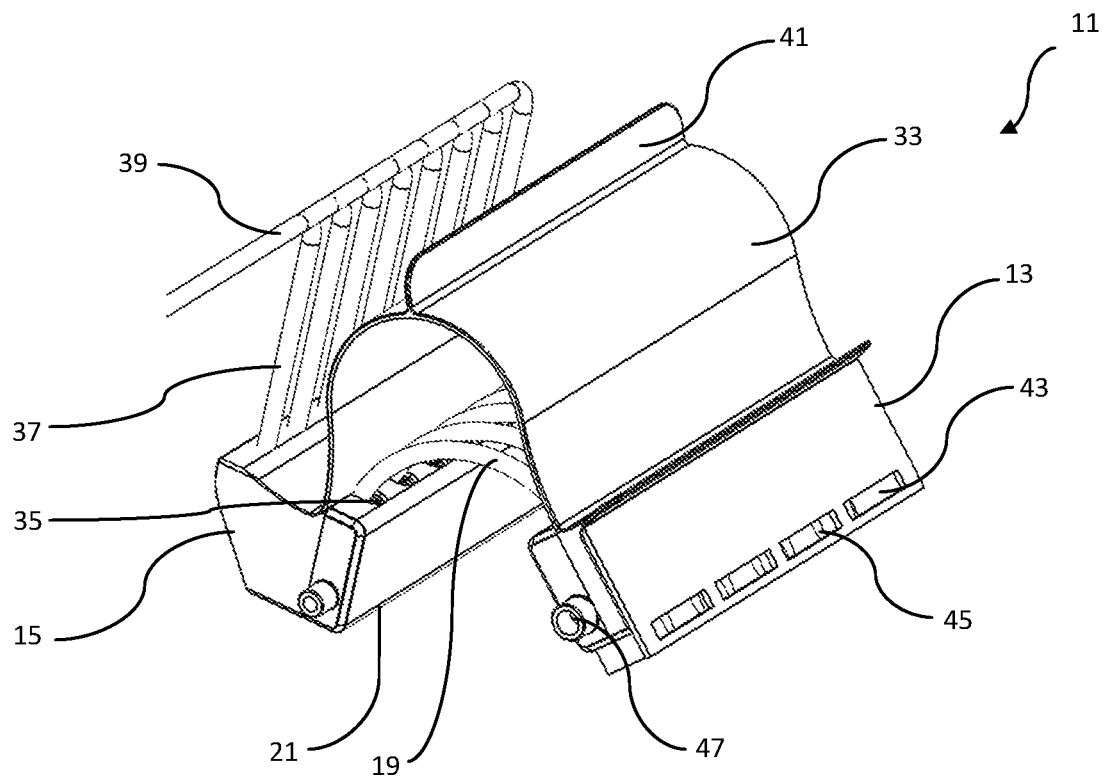
FIG. 2 shows a three-dimensional view of a dispenser cassette according to the invention, with 8 tubes.

A dispenser cassette 11 according to the invention is shown in FIG. 2. Unlike the dispenser cassette 11 from the prior art, a first cartridge 13 is connected to a second cartridge 15 by means of an elastic connector 33. There is no third cartridge 17, as is the case in the prior art. The function of the third cartridge 17 is assumed by second cartridge 15 in the dispenser cassette 11 according to the invention. The first and second cartridges 15, 17 are box-shaped components, with longitudinal edges 21 that are multiples of the other two edges. The cartridges 13, 15 are arranged such that their longitudinal edges 21 are parallel. Both cartridges 13, 15 have openings on their upper surfaces, through which tubes are fed. The first cartridge 13 is wider than the second cartridge 15. The second cartridge 15 accommodates not only the tubes 19 to the first cartridge, but also the feed tubes 37. The number of feed tubes is equal to the number of tubes 19 between the first and second cartridges 13, 15. The feed tubes 37 are perpendicular to the upper surface of the cartridge. They all branch off of a main tube 39, which is parallel to the longitudinal edges 21 of the cartridges. The function of the main tube 39 is to convey the medium that is to be dispensed from a container (not shown) to the feed tubes 37. It is also conceivable that the feed tubes 37 draw the medium to be dispensed directly from the container, such that there would be no need for the main tube. One advantage with this embodiment without a main tube would be the possibility of controlling or operating the feed tubes individually.

The connector 33 is a U-shaped component, which is connected at each end to a cartridge 13, 15. The width of the connector is basically the same as the longitudinal edge of the cartridge 21. The width of the connector is placed on the upper surface of the cartridges, in the middle, on the longitudinal side. The connector 33 is rectangular when not curved, wherein the length and width are multiples of the height.

The connector 33 comprises an elastic material, which can be deformed such that the ends of the connector 33 can move toward one another with the cartridges attached thereto. The connector 33 has a ridge 41 in the middle. This runs on the side of the connector facing away from the interior of the U-shaped component parallel to the longitudinal edges 21 of the cartridges. The thickness of the ridge 41 is the same as the thickness of the elastic connector 33 in its other regions. The height of the ridge 41 is such that it can be held by a person's fingers.

The first cartridge 13 has holes 43 on its longitudinal side facing outward. The holes 43 are near the edge but well above the longitudinal edge. The holes 43 are repeatedly interrupted by webs in the longitudinal direction of the cartridge 25. Nozzle tips 45 can be seen in the holes. Each nozzle tip 45 in the first cartridge 13 is connected in a sealed manner to a tube 19, such that the nozzle tip 45 can receive and convey the medium from the tube 19 without any substantial losses.

Figure 3:
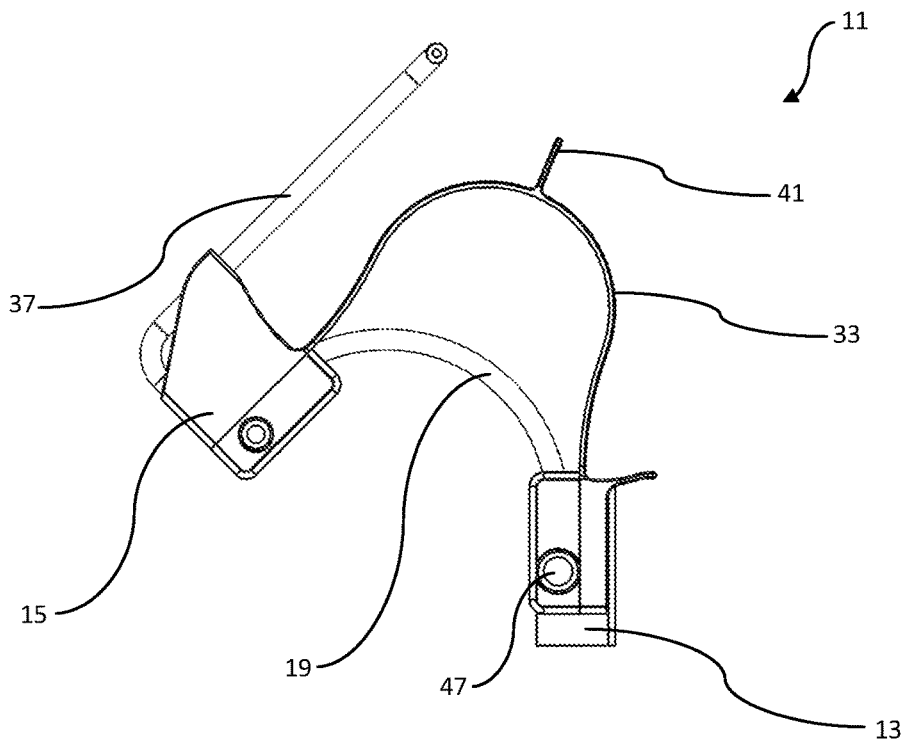
FIG. 3 shows a side view of a dispenser cassette, which is ready to be installed in a peristaltic pump.

A dispenser cassette 11 is shown from the side in FIG. 3. The tubes 19 between the first and second cartridges 13, 15 are shorter than the connector 33. As a result, the tubes are always located within the interior region formed by the U-shaped component. The edges of both cartridges 13, 15 are beveled. A cylindrical projection 47 is attached to the sides of both cartridges shown in FIG. 3. The cylindrical axis of the projection 47 is parallel to the longitudinal edge 21 of the cartridge. The projection 47 comprises a recess in the middle, such that the projection 47 is formed by a cylindrical wall. The projection 47 on the first cartridge 13 is larger than that on the second cartridge 15. The projection 47 can function as a latching element for connecting to a peristaltic pump.

Unlike the dispenser cassettes 11 from the prior art, the dispenser cassette 11 shown in FIG. 3 does not need to have a tensioning element for adjusting the tension acting on a tube. The preferred combination of a dispenser cassette shown in FIG. 2 and FIG. 3 is that with tubes that have such a small variation in diameters that the same tension can be applied to all of the tubes.

Figure 4:
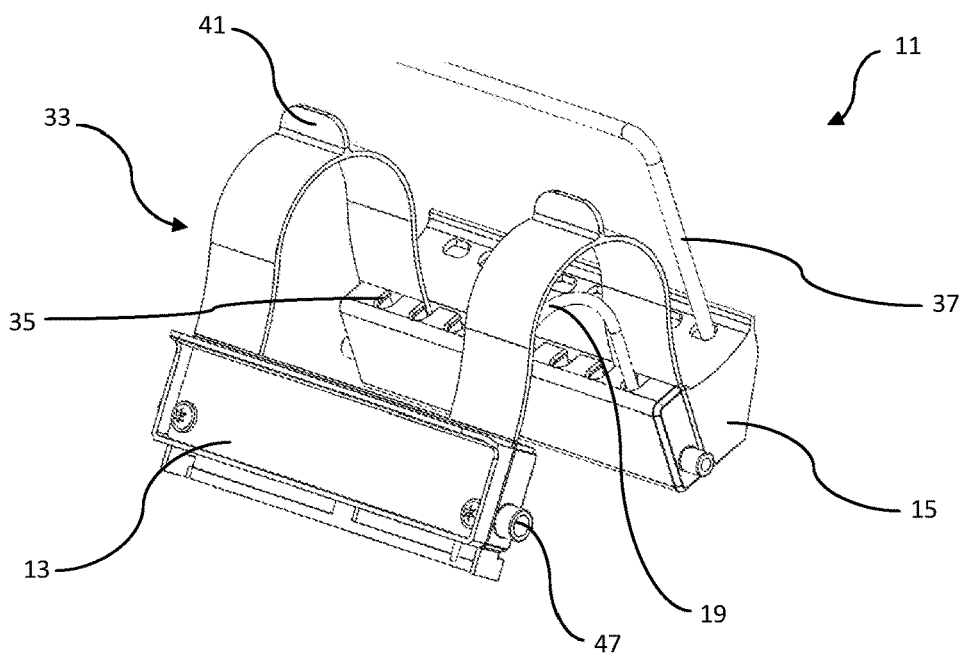
FIG. 4 shows a three-dimensional view of the dispenser cassette according to the invention, with a two-part connector.

A dispenser cassette 11 with a different design for the elastic connector 33 is shown in FIG. 4. This connector comprises two parts. The cartridges 13, 15 and the tubes are the same. Unlike the connector 33 shown in FIGS. 2 and 3, the connector 33 in FIG. 4 is not as long as the cartridges 13, 15, extending instead over a smaller area at the two ends of the cartridges 13, The shape of the connector 33 in FIG. 4 is the same as that in FIGS. 2 and 3, aside from the width. The width of the connector is reduced to a fifth or sixth of the original size, such that the connector can be formed by two parts, as shown in the embodiment in FIG. 4. It is conceivable that the connector is also comprised of numerous parts. These parts must then be narrow enough that all of them can be placed on a side of the cartridge. Even with a multi-part construction, the width of the elastic connector is preferably 10%, more preferably 15% of the length of the cartridge.

FIG. 4 simply shows a tube connection from the feed tube to the nozzle. When using the dispenser cassette 11, it can be assumed that the other tubes can also be attached to the dispenser cassette 11. If the elastic connector 33 is composed of numerous pieces, the elastic connector 33 may not cover all of the tubes 19. With the two-part construction of the connector 33 shown in FIG. 4, the cartridges 13, 15 can be twisted in relation to one another with less resistance than with a one-piece construction of the elastic connector 33. This is enabled by placing the parts of the elastic connector 33 at the ends of the cartridges 13, 15, which are also not connected to one another.

Figure 5:
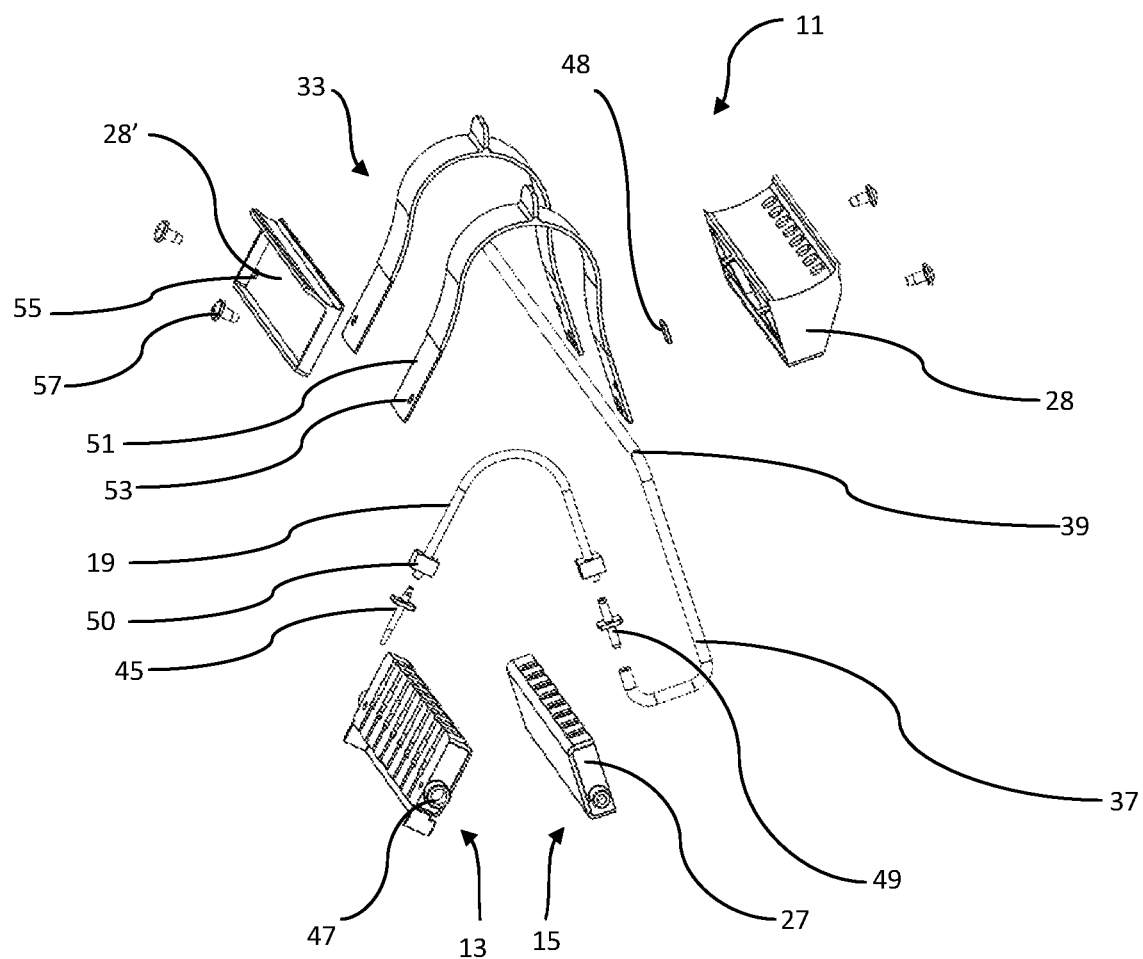
FIG. 5 shows an exploded view of a dispenser cassette with a two-part connector.

And exploded view of a dispenser cassette 11 is shown with its most important components in FIG. 5. The cartridges 13, 15 have a two-piece construction, like that from the prior art. The container 27 for the cartridges is formed by the part that receives the tubes. The second part forms the lid 28, which is placed on the container 27 such that the tubes 19 are fixed in position by it. The tube connection comprises a main tube 39, a feed tube 37, and a tube 19 located between the two cartridges. Only one tube connection is shown in the exploded view. More tube connections may be used in the application, however, although this does not alter the number of main tubes 39, which remains 1. A connecting piece 49 is located between the feed tube 38 and the tube between the cartridges 13, 15. It comprises a short tube segment, the outer wall of which is conical at both ends. Each end of the connecting piece 49 can be inserted into one of the connecting tubes. When the tube is pulled over the connecting piece 49, a frictional connection is obtained, due to the conical shape of the outer wall of the connecting piece, and the elasticity of the tube. A nozzle 45 can be attached to the other end of the tube 19. Like the connecting piece, it also has a conical outer wall, so that it can also be inserted into the tube 19. Both the outer and inner diameters of the end of the nozzle opposite the tube are reduced. This reduces the cross section area, blocking the dispensing of residual droplets of the liquid. The tube 19 has a radial reinforcement 50 at both ends. The reinforcements 50 have a square cross section, and are approximately two to three times as big as the cross section of the tube 19. There are holes in the cartridges 13, 15, which cannot be seen in FIG. 5, in which the reinforcements of the tubes are inserted. This results in a form-fitting connection between the tubes 19 and the cartridges 13, such that the tube is secured in the respective cartridge 13, 15.

There is an RFID tag 48 in the second cartridge 15. The RFID tag can contain information relating to the operation of the dispenser cassette 11, e.g. the pump factor. The information in the RFID tag can be transmitted wirelessly to a neighboring component. This component can be the peristaltic pump in which the dispenser cassette is located, for example.

The elastic connector 33 comprises to parts in FIG. 5, like that in FIG. 4. These have extensions 51 at each end, which are not visible in the assembled state. There is hole 53 in each of these extensions 51. There are also holes 55 in the lids 28, 28' for the two cartridges 13, such that in the assembled state of the dispenser cassette 11, the holes in the lid of the cartridge are aligned with the hole 53 in the elastic connector. A screw 57 is then inserted into the hole, holding the cartridge in place in the container 27, and thus holding all of the components together.

LIST OF REFERENCE SYMBOLS 11 dispenser cassette
13 first cartridge
15 second cartridge
17 third cartridge
19 tube
21 longitudinal edge of the cartridge
23 width of the cartridge
25 seat for placing the tubes
27 container for the cartridge 28, 28' lid for the cartridge
29 opening in the container for the cartridge
31 tensioning element
33 elastic connector
35 opening on the upper surface of the cartridge
37 feed tube
39 main tube
41 ridge on the connector
43 lateral holes in the first cartridge
45 nozzle tip
47 cylindrical projection/latching element
48 RIFD tag
49 connecting piece
50 reinforcements on the tubes
51 extension of the elastic connector
53 hole in elastic connector
55 hole in lid for the cartridge
57 screw

What is claimed is:

1. A dispenser cassette (11) that releasably attaches to a peristaltic pump, said dispenser cassette comprising:
    an output cartridge (13) that is adapted to be mounted to the peristaltic pump;
    an intake cartridge (15) that is adapted to be mounted to the peristaltic pump;
    pumping tubes (19), which are accommodated in the dispenser cassette (11) such that an output end of each pumping tube is inserted in the output cartridge and an intake end of each pumping tube is inserted into the intake cartridge;
    an elastic connector (33) connected between the output cartridge and the intake cartridge such that the output cartridge and intake cartridge are able to move in relation to one another, said pumping tubes between the output and intake cartridges being shorter than the elastic connector such that the elastic connector is located apart from the pumping tubes and lies outside of the pumping tubes; and
    nozzles for dispensing liquid from the pumping tubes, wherein each nozzle is attached on the output end of the respective pumping tube inside the output cartridge;
    wherein, when the dispenser cassette is attached to the peristaltic pump and rotors in the peristaltic pump are rotating to pump liquid, the pumping tubes are stretched over the rotors and liquid is conveyed through the pumping tubes by external deformation of the pumping tubes by the rotors without pressing the pumping tubes against a wall, and the liquid is dispensed through each pumping tube through the respective nozzle.

2. The dispenser cassette (11) according to claim 1, wherein the elastic connector (33) is U-shaped.

3. The dispenser cassette (11) according to claim 1, wherein the pumping tubes (19) are releasably attached to the two cartridges (13, 15).

4. The dispenser cassette (11) according to claim 1, wherein the output cartridge has the same number of holes for pumping tubes and nozzles.

5. The dispenser cassette (11) according to claim 1, wherein the pumping tubes (19) span a U-shaped curve in the dispenser cassette.

6. The dispenser cassette (11) according to claim 1, wherein the output cartridge includes means for mounting the output cartridge to the peristaltic pump and the intake cartridge includes means for mounting the intake cartridge to the peristaltic pump.

7. The dispenser cassette (11) according to claim 1, wherein the intake cartridge (15) receives one or more feed tubes (37), that supplies liquid to the dispenser cassette (11).

8. The dispenser cassette (11) according to claim 1, wherein the number of feed tubes (37) is equal to the number of pumping tubes (19) between the cartridges (13, 15) in the dispenser cassette (11), such that the contents of a given feed tube (37) within the intake cartridge (15) are transferred to an associated pumping tube (19).

9. The dispenser cassette (11) according to claim 6, wherein the width of the dispenser cassette (11) is 15 cm, and the elastic connector is adapted to be held by a user such that the dispenser cassette can be attached to a peristaltic pump with one hand.

10. The dispenser cassette (11) according to claim 1, wherein the dispenser cassette (11) comprises an RFID module, which can communicate with the peristaltic pump.

11. The dispenser cassette (11) according to claim 1, wherein the dispenser cassette (11) can accommodate up to 32 pumping tubes (19).

12. The dispenser cassette (11) according to claim 1, wherein the pumping tubes are capable of being removed from the output and intake cartridges, and the ends of the pumping tubes (19) have reinforcements (50), which can be received in tube retaining holes in the cartridges (13, 15).

13. The dispenser cassette (11) according to claim 1, wherein the pumping tubes (19) are parallel to one another in the dispenser cassette (11), and each have the same length and inner and outer diameter.

14. The dispenser cassette (11) according to claim 1, wherein the pumping tubes (19) are permanently attached to the two cartridges (13, 15).

15. The dispenser cassette (11) according to claim 14, wherein the pumping tubes (19) are materially bonded to the two cartridges (13, 15).

* * * * *